United States Patent
Guez et al.

(10) Patent No.: US 6,653,336 B1
(45) Date of Patent: Nov. 25, 2003

(54) COMBINATION OF HYPERTENSIN CONVERTING ENZYME INHIBITOR WITH A DIURETIC FOR TREATING MICROCIRCULATION DISORDERS

(75) Inventors: David Guez, Neuilly sur Seine (FR); Pierre Schiavi, Nanterre (FR); Bernard Levy, Paris (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/554,715

(22) PCT Filed: Mar. 3, 1998

(86) PCT No.: PCT/FR98/00411
§ 371 (c)(1),
(2), (4) Date: May 18, 2000

(87) PCT Pub. No.: WO99/25374
PCT Pub. Date: May 27, 1999

(30) Foreign Application Priority Data

Nov. 19, 1997 (FR) .............................. 97 14485

(51) Int. Cl.[7] .............................. A61K 31/40

(52) U.S. Cl. .................. 514/410; 514/412; 514/415; 514/423; 514/426

(58) Field of Search .................. 514/410, 412, 514/415, 423, 426

(56) References Cited

U.S. PATENT DOCUMENTS 5,686,451 A * 11/1997 Kristianson et al. ..... 514/223.5

OTHER PUBLICATIONS

Parving, Journal of Cardiovascular Pharmacology, 19 (Suppl. 6) S19–S24 (1992).*
Luccioni et al., Journal of Hypertension, 13 (12 Part 2), (1995), 1847–1851, abstract only.*

* cited by examiner

Primary Examiner—Raymond Henley, III
Assistant Examiner—C. Delacroix-Muirheid
(74) Attorney, Agent, or Firm—The Firm of Hueschen and Sage

(57) ABSTRACT

The present invention relates to the use of a combination of an antiotensin-converting enzyme inhibitor (CEI) and of a diuretic for the treatment of arteriolo-capillary microcirculatory disorders and to pharmaceutical compositions containing the same.

9 Claims, No Drawings

COMBINATION OF HYPERTENSIN CONVERTING ENZYME INHIBITOR WITH A DIURETIC FOR TREATING MICROCIRCULATION DISORDERS

The present application is a U.S. National Application filed under 35 USC 371 of PCT/FR98/00411, filed Mar. 3, 1998 based upon French Application Serial No. 97.14485 filed Nov. 19, 1997.

The present invention relates to the use of a combination of an angiotensin converting enzyme inhibitor (CEI) and of a diuretic for producing pharmaceutical compositions intended for the treatment of arteriolo-capillary microcirculatory disorders.

It is known that the majority of degenerative vascular diseases, for example arterial hypertension (N. M. Kaplan, "*Microvascular Rarefaction*", Clinical Hypertension, 6$^{th}$ Ed., Baltimore, Wilkinson and Wilkins, 1994, 86; A. S. Greene et al., "*Microvascular rarefaction and tissue vascular resistance in hypertension*", Am. J. Physiol., 1989, 256 (Heart Circ. Physiol., 25), H 126-H 31; A. S. Izzard et al., "*Hypertension and the vasculature: arterioles and the myogenic response*", J. Hypertens., 1995, 13, 1–4; A. M. Heagerty et al., "*Small artery structure in hypertension*", Hypertension, 1993, 21, 391–7), but also vascular complications of certain metabolic diseases, for example diabetes mellitus (G. Reach et al., "*Causes et mécanismes de la microangiopathie et de la neuropathie—L'hypothèse glucose" et ses implications* [Causes and mechanisms of microangiopathy and neuropathy—"The glucose hypothesis" and its implications]", in: G. Tchobroutsky, G. Slama, R. Assan, P. Freychet, Paris: Pradel, 1990, 448–57), or certain dyslipidemias (J. F. Toole, "*Atherosclerosis*", Cerebrovascular Disorders, New York, Raven Press, 1984, 199–213) are accompanied by detrimental anatomical and/or functional changes in the arteriolo-capillary microcirculation (J. C. M. L. Le Noble et al., "A functional morphometric study of the cremaster muscle microcirculation in young spontaneously hypertensive rats", J. Hypertens., 1990, 8,741–8; I. I. H. Chen et al., "*Microvascular rarefaction in spontaneously hypertensive rat cremaster muscle*", Am. J. Physiol., 1981, 241, H 306–10).

The detrimental anatomical and/or functional changes in the arteriolo-capillary microcirculation can take different forms, such as, for example:

- an arteriolo-capillary rarefaction (P. Gasser, "*Nailfold microcirculation in normotensive and essential hypertensive subjects as assessed by video-microscopy*", J. Hypertens., 1992, 1, 83–6),
- a lack of arteriolo-capillary recruitment (B. W. Zweifach, "*Micropressure-flow relationships in a skeletal muscle of spontaneously hypertensive rats*", Hypertension, 1981, 3, 601–14),
- and, more generally, poor adjustment of the distribution of the blood in the tissues to metabolic requirements, any detrimental change capable of inducing or perpetuating a tissue hypoperfusion or an ischemia, absolute or relative (E. Vicaut, "*Hypertension and the microcirculation: a brief overview of experimental studies*", J. Hypertens., 1992, 10, suppl. 5, S59–S68).

It is also known that the detrimental anatomical and/or functional changes in the arteriolo-capillary microcirculation described above can precede, for example, the rise in pressure values in arterial hypertension, creating for some a true vicious circle (A. J. Zweifler et al., "*Diminished finger pulse in borderline hypertension: evidence for early structural vascular abnormality*", Am. Heart J., 1982, 104, 812–15; J. M. Sullivan et al., "*Attenuation of the microcirculation in young patients with high-output borderline hypertension*", Hypertension, 1983, 5, 844–51).

Finally, it is known that a great many factors are involved simultaneously in the regulation of general hemodynamics (outputs, resistances, pressures, and the like) and in the regulation, or rather adjustment, of the distribution of blood in the tissues according to the context (hierarchization depending on the nature of the organs, and the like) and the metabolic requirements of the moment (M. J. Mulvany, "*The structure of the resistance vasculature in essential hypertension*", J. Hypertens., 1987, 5, 129:H; H. A. J. Struijker-Boudier et al., "*The microcirculation and hypertension*", J. Hypertens., 1992, 10 (suppl. 7), S147–S156).

A great many vasoactive substances have been identified, with very particular interest in recent years in, by way of example, substances originating from or having an effect on smooth muscle fibers and the vascular endothelium (S. Laurent et al., "*Physiopathologie et pharmacologie du remodelage artériel dans l'hypertension artérielle* [Physiopathology and pharmacology of arterial remodeling in arterial hypertension]", the letter from the pharmacologist, 1997, 11, 146–54; Taddei et al., "*Hypertension causes prematurate* [sic] *aging of endothelial function in humans*", Hypertension, 1997, 29, 736–43).

The complexity of these different regulations, the number of factors involved and their interactivity, better understood today, have led us to provide the combination of several medicaments, directly or indirectly vasoactive, for both preventing and treating:

- on the one hand, the clinical attack, for example arterial hypertension, when the rise in pressure values reaches, or indeed exceeds, the standards recommended by the international scientific community;
- on the other hand, its repercussions on tissue perfusion in the context of macro/microcirculatory disorders which, it is known, can precede, maintain and aggravate the clinical entity described above by way of example (arterial hypertension but also, for example, vascular complications of certain metabolic diseases, and the like) (H. A. J. Struijker-Boudier et al., "*Assessment of the microcirculation in cardiovascular disease*", Clin. Sci., 1996, 91, 131–9).

The actions of different vasoactive substances can thus usefully complement one another and provide an improved therapeutic effect in the basic treatment of degenerative vascular diseases, or indeed in the prevention of the incidents and accidents which they induce.

It is also known that some CEIs have a beneficial effect on arteriolar or coronary microcirculation but at no time has a beneficial effect on the functional unit represented by an arteriola and the adjacent capillaries been demonstrated in the literature.

It has now been shown, which is the subject of the present invention, that the combination of a CEI with a diuretic, in addition to the known properties of this combination, made it possible, surprisingly, to correct microcirculatory disorders at both the arteriolar and capillary level, whereas no property of this nature had ever been described or claimed in prior publications or patents relating to combinations, in particular of CEI and of diuretics, to CEIs or to diuretics.

The novelty of this type of combination of vasoactive agents lies in addition in the fact, in particular, that each of the constituents of the combination is generally used at low doses, generally lower than those used in each of their first indications.

The usefulness of this type of combination thus lies in the production of pharmaceutical compositions of use in the treatment of arteriolo-capillary micro-circulatory disorders. These compositions can thus be used in all pathologies where microcirculatory disorders are involved, such as, for example, degenerative vascular diseases, arterial hypertension, cardiac insufficiency, cerebral ischemia, heart attacks, arteritis of the lower limbs, the prevention and treatment of cardiovascular complications of type-II diabetes, retinopathies, nephropathies, and the like, as main or secondary treatment.

The CEIs which can be used in these compositions are, without implied limitation: Perindopril, Captopril, Enalapril, Lisinopril, Delapril, Fosinopril, Quinapril, Ramipril, Spirapril, Imidapril, Trandolapril, Benazepril, Cilazapril and Temocapril, and their addition salts with a pharmaceutically acceptable acid orbase.

The preferred CEIs are Perindopril, Captopril, Enalapril, Lisinopril, Benazapril, Quinapril and Delapril and their salts and more particularly Perindopril and its salts.

The diuretics which can be used in these compositions are, without implied limitation: Indapamide, Hydrochlorothiazide, Furosemide, Altizide, Trichlormethiazide, Triflumethazide, Bemetizide, Cyclothiazide, Methylclothiazide, Azosemide, Chlorothiazide, Butizide, Bendrofluazide, Cyclopenthiazide, Benzchlortriazide, Polythiazide, Hydroflumethiazide, Benzthiazide, Ethiazide, Penflutazide, Clopamide, Cicletanide or Piretanide, and their addition salts with a pharmaceutically acceptable acid or base.

The preferred diuretics are Indapamide and Hydrochlorothiazide and their salts and more particularly Indapamide and its salts.

The invention thus more preferably relates to the use of a combination of the converting enzyme inhibitor Perindopril or one of its addition salts with a pharmaceutically acceptable base and of the diuretic Indapamide in order to obtain pharmaceutical compositions intended for the treatment of arteriolo-capillary microcirculatory disorders.

The pharmaceutical compositions according to the invention will be presented in pharmaceutical forms suitable for administration by the oral, parenteral and in particular intravenous, per- or transcutaneous, nasal, rectal, perlingual, ocular or respiratory route and more specifically tablets, sublingual tablets, capsules, including hard gelatin capsules, glossettes, lozenges, injectable preparations, aerosols, eye or nose drops, suppositories, creams, ointments, dermal gels, and the like.

The preferred administration route is the oral route and the corresponding pharmaceutical compositions which allow the instantaneous or delayed release of the active principles.

Tablets are the preferred pharmaceutical compositions.

In the pharmaceutical compositions according to the invention, the amounts of CEI and of diuretic are adjusted to the nature of these active principles and their relative proportions thus vary with the active principles.

When the CEI is Perindopril in the tert-butylamine salt form and when the diuretic is Indapamide, these proportions are respectively between 65 and 85% and between 35 and 15% of the total mass of the active principles and preferably between 70 and 80% for the CEI and between 30 and 20% for the diuretic.

The preferred percentages for this combination are 76% of tert-butylamine salt of Perindopril and 24% of Indapamide.

The compositions according to the invention, in addition to the active principles, contain one or more pharmaceutically acceptable vehicles or excipients.

Mention may be made, among pharmaceutically acceptable excipients, without implied limitation, of binders, diluents, disintegrating agents, stabilizing agents, preservatives, lubricants, fragrances, flavoring agents or sweeteners.

The posology varies according to the age and weight of the patient, the administration route or the nature of the therapeutic indication and of the associated treatments. It ranges between 1 and 50 mg according to the nature of the CEI and between 0.5 and 25 mg according to the nature of the diuretic, taken one or more times per 24 hours.

Examples of pharmaceutical compositions according to the invention. The examples are given without implied limitation.

EXAMPLE 1

Perindopril/Indapamide Tablets

| Constituents | Amount (mg) |
| --- | --- |
| Perindopril, tert-butylamine salt | 2 |
| Indapamide | 0.625 |
| Hydrophobic colloidal silica | 0.25 |
| Lactose | 64.175 |
| Magnesium stearate | 0.45 |
| Microcrystalline cellulose | 22.5 |
| For a tablet completed to | 90 |

EXAMPLE 2

| Constituents | Amount (mg) |
| --- | --- |
| Perindopril, tert-butylamine salt | 4 |
| Indapamide | 1.25 |
| Hydrophobic colloidal silica | 0.25 |
| Lactose | 61.55 |
| Magnesium stearate | 0.45 |
| Microcrystalline cellulose | 22.5 |
| For a tablet completed to | 90 |

EXAMPLE 3

| Constituents | Amount (mg) |
| --- | --- |
| Captopril | 50 |
| Hydrochlorothiazide | 25 |

EXAMPLE 4

| Constituents | Amount (mg) |
| --- | --- |
| Enalapril, maleate | 20 |
| Hydrochlorothiazide | 12.5 |

EXAMPLE 5

| Constituents | Amount (mg) |
|---|---|
| Lisinopril | 20 |
| Hydrochlorothiazide | 12.5 |

EXAMPLE 6

| Constituents | Amount (mg) |
|---|---|
| Benazepril, hydrochloride | 10 |
| Hydrochlorothiazide | 12.5 |

EXAMPLE 7

| Constituents | Amount (mg) |
|---|---|
| Quinapril, hydrochloride | 20 |
| Hydrochlorothiazide | 12.5 |

EXAMPLE 8

| Constituents | Amount (mg) |
|---|---|
| Perindopril, tert-butylamine salt | 2 |
| Hydrochlorothiazide | 12.5 |

EXAMPLE 9

| Constituents | Amount (mg) |
|---|---|
| Perindopril, tert-butylamine salt | 4 |
| Hydrochlorothiazide | 25 |

EXAMPLE 10

| Constituents | Amount (mg) |
|---|---|
| Captopril | 50 |
| Indapamide | 1.25 |

EXAMPLE 11

| Constituents | Amount (mg) |
|---|---|
| Enalapril, maleate | 20 |
| Indapamide | 1.25 |

EXAMPLE 12

| Constituents | Amount (mg) |
|---|---|
| Lisinopril | 20 |
| Indapamide | 1.25 |

EXAMPLE 13

| Constituents | Amount (mg) |
|---|---|
| Benazepril, hydrochloride | 10 |
| Indapamide | 1.25 |

EXAMPLE 14

| Constituents | Amount (mg) |
|---|---|
| Quinapril, hydrochloride | 20 |
| Indapamide | 1.25 |

EXAMPLE 15

| Constituents | Amount (mg) |
|---|---|
| Perindopril, tert-butylamine salt | 4 |
| Bendrofluazide | 5 |

EXAMPLE 16

| Constituents | Amount (mg) |
|---|---|
| Captopril | 50 |
| Bendrofluazide | 5 |

EXAMPLE 17

| Constituents | Amount (mg) |
|---|---|
| Delapril, hydrochloride | 30 |
| Indapamide | 2.5 |

EXAMPLE 18

| Constituents | Amount (mg) |
|---|---|
| Delapril, hydrochloride | 30 |
| Hydrochlorothiazide | 25 |

EXAMPLE 19

| Constituents | Amount (mg) |
| --- | --- |
| Fosinopril | 10 |
| Hydrochlorothiazide | 25 |

Pharmacological Study of the Compositions According to the Invention

Effects of the combination of the tert-butylamine salt of Perindopril (0.76 mg/kg/d, PO)+Indapamide (0.24 mg/kg/d, PO) on the 1R-1C reno-vascular hypertensive rat: Hemodynamic aspect and studies of the subendocardial arteriolo-capillary density.

Wistar rats aged 8 weeks (n=56; body weight=200 g) were firstly subjected to the positioning of a clip (0.2 mm in diameter) on the left renal artery and, four days later, a contralateral nephrectomy was carried out. A series of identical rats (n=13) was subjected to the same interventions (anesthesia+surgery) but without stenosis of the renal artery or nephrectomy (NT control group). 1R-1C Goldblatt rats received:

- either a normal feed: HT control group;
- or a feed containing tert-butylamine salt of perindopril (0.76 mg/kg/day) and indapamide (0.24 mg/kg/day): HT group+combination.

The numbers in each group were adjusted, taking into account the specific mortality in each group, so as to be able to analyze, after treatment for 4 weeks, at least 9 animals per group.

|  | Numbers operated upon | Analyzed (survivors) |
| --- | --- | --- |
| NT Control | 13 | 13 |
| HT Control | 21 | 9 |
| HT + Perindopril-Indapamide combination | 18 | 10 |

After treatment for 4 weeks, the hemodynamic parameters were recorded under anesthesia (Table I) and then the heart was removed for quantitative histomorphometric analysis. The Perindopril salt-Indapamide combination significantly decreased the arterial pressure ($p<0.01$). The cardiac output and the heart rate were not modified by the treatment. The degree of left ventricular hypertrophy (weight of the LV/body weight) was significantly decreased with respect to the HT control group ($p<0.001$).

TABLE I

|  | NT Control | HT Control | HT + combination |
| --- | --- | --- | --- |
| Systolic arterial pressures (mm Hg) | 138 ± 5 | 209 ± 12 | 110 ± 19 |
| Diastolic arterial pressures (mm Hg) | 110 ± 5 | 146 ± 11 | 79 ± 12 |
| Cardiac output (ml/min) | 59 ± 4 | 45 ± 4 | 63 ± 7 |
| Heart rate( /min) | 486 ± 10 | 455 ± 19 | 496 ± 11 |
| LV weight/Body weight (mg/g) | 2.1 ± 0.1 | 3.7 ± 0.2 | 2.2 ± 0.2 |

Subendocardial Capillary Density in the Wall of the Left Ventricle

The capillary density was significantly decreased in the HT control group in comparison with the NT control group ($p<0.05$) and normalized by the Perindopril salt-Indapamide combination.

Subendocardial Arteriolar density in the Wall of the left Ventricle

The number of arteriolae per $mm^2$ of subendocardial surface was significantly increased in the HT control group ($p<0.05$) and normalized in the Perindopril salt-Indapamide combination group.

The results are presented in Table II.

TABLE II

| ($n/mm^2$) | NT Control | HT Control | HT + Combination |
| --- | --- | --- | --- |
| Subendocardial capillary density | 1030 ± 42 | 916 ± 39 | 1076 ± 41 |
| Subendocardial arteriolar density | 8.25 ± 0,46 | 10.51 ± 0.41 | 8.96 ± 0.63 |

The preceding data may thus be interpreted in the following way:

It is confirmed that there exists in the majority of degenerative vascular diseases, in this instance in arterial hypertension, detrimental anatomical and/or functional changes in the arteriolo-capillary microcirculation.

In the experiment carried out here, the most marked anomaly relates to the capillary density, which is greatly decreased in the hypertensive subjects and normalized under the effect of the "treatment" by the combination of these two active principles.

The respective share of the effect of each of the constituents of the combination on the arteriolae and the capillaries is, on account of the conditions under which the experiment was carried out, difficult to define. However, it seems that each of the constituents has a role both with respect to the arteriolar component and the capillary component of the microcirculatory functional unit.

In conclusion, the fact of combining the Perindopril salt and Indapamide, in the proportions 76/24%, normalizes the subendocardial capillary and arteriolar densities studied here in order to illustrate the invention.

What is claimed is:

1. A method for the treatment of an arteriolo-capillary microcirculatory disorder, other than arterial hypertension, cardiac insufficiency, and nephropathy, in a living animal comprising the step of administering to the living animal an amount of a combination of an angiotensin-converting enzyme inhibitor and a diuretic which is effective for alleviation of said disorder.

2. The method as claimed in claim 1, wherein the converting enzyme inhibitor is selected from Perindopril, Captopril, Enalapril, Lisinopril, Delapril, Fosinopril, Quinapril, Ramipril, Spirapril, Imidapril, Trandolapril, Benazepril, Cilazapril and Temocapril and wherein the diuretic selected from Indaparride, Hydrochlorothiazide, Furosemide, Altizide, Trichlormethiazide, Triflumethazide, Bemetizide, Cyclothiazide, Methylclothiazide, Azosemide, Chlorothiazide, Butizide, Bendrofluazide, Cyclopenthiazide, Benzchlortriazide, Polythiazide, Hydroflumethiazide, Benzthiazide, Ethiazide, Penflutazide, Clopamide, Cicletanide and Piretanide, or the addition salts of any of the foregoing compounds with a pharmaceutically-acceptable acid or base.

3. The method as claimed in claim 2, wherein the converting enzyme inhibitor is selected from Perindopril, Captopril, Enalapril, Lisinopril, Benazepril, Quinapril and Delapril and wherein the diuretic is selected from Indapamide and Hydrochlorothiazide, or and the addition salts of any of the foregoin compounds with a pharmaceutically-acceptable acid or base.

4. The method of claim 3 wherein the converting enzyme inhibitor is Perindopril or one of its addition salts with a pharmaceutically-acceptable base and wherein the diuretic is Indapamide.

5. The method as claimed in claim 4, wherein the converting enzyme inhibitor is the tert-butylamine salt of Perindopril and wherein the diuretic is Indapamide.

6. The method as claimed in claim 4, wherein the administration is of a pharmaceutical composition containing amounts of the tert-butylamine salt of Perindopril and of Indapamide respectively of between 65 and 85% and between 35 and 15% of the total mass of the active principles.

7. The method as claimed in claim 6, wherein these amounts are 76% of the tert-butylamine salt of Perindopril and 24% of Indapamide.

8. The method as claimed in claim 6, wherein the pharmaceutical composition is in tablet form.

9. The method as claimed in claim 1, wherein the administration is of a pharmaceutical composition containing both active ingredients.

* * * * *